United States Patent [19]

Bergersen

[11] Patent Number: 5,645,420
[45] Date of Patent: Jul. 8, 1997

[54] MULTI-RACIAL PREFORMED ORTHODONTIC TREATMENT APPLICANCE

[75] Inventor: Earl O. Bergersen, Winnetka, Ill.

[73] Assignee: Ortho-Tain, Inc., Bayamon, Puerto Rico

[21] Appl. No.: 407,919

[22] Filed: Mar. 21, 1995

Related U.S. Application Data

[63] Continuation of Ser. No. 89,577, Jul. 12, 1993, abandoned.
[51] Int. Cl.$^6$ .................................................... A61C 3/00
[52] U.S. Cl. .................................................... 433/6
[58] Field of Search ........................... 433/6, 24; 128/861

[56] References Cited

U.S. PATENT DOCUMENTS

| | | | |
|---|---|---|---|
| 3,478,429 | 11/1969 | Shilliday | 433/6 |
| 4,504,225 | 3/1985 | Yoshii | 433/6 |
| 5,028,231 | 7/1991 | Hall | 433/6 |
| 5,059,118 | 10/1991 | Breads et al. | 433/6 |
| 5,259,762 | 11/1993 | Farrell | 433/6 X |

*Primary Examiner*—Nicholas D. Lucchesi
*Attorney, Agent, or Firm*—Hill, Steadman & Simpson

[57] ABSTRACT

An orthodontic appliance of the type which is generally U-shaped in plan view and includes a tooth receiving trough formed between lingual and labial/buccal side flanges in at least one of the upper or lower sides thereof is provided for use by Caucasoid, Mongoloid and Negroid patients. The trough includes tooth receiving depressions for receiving and positioning teeth from central and lateral incisors to and including a molar. The appliance preferably is preformed in a range of different sizes to accommodate different sized mouths and stages of dentition. The troughs, when two are provided, may be vertically fixed relative to one another in that the appliance is a single body device or may be movable relative to one another and joined at a pair of posterior hinges. The labial flange, in an area of the incisors, extends gingivally from a tooth receiving surface of said trough by more than 10 mm so as to overlie a patient's gingival labial tissue and pre-maxilla to an extent not previously provided and up to 10 mm further gingivally on the lingual in the area of the four lower incisors. Further, the lingual flange defining the upper trough has lingually extending depressions of 0.1 to 1 mm which extend slightly laterally at a mesial area and distal edge of the central incisors and at a distal edge and a mesial edge of the lateral incisors so as to be positioned adjacent to the lateral edges of all four incisors.

36 Claims, 2 Drawing Sheets

MULTI-RACIAL PREFORMED ORTHODONTIC TREATMENT APPLICANCE

This is a continuation, of application Ser. No. 08/089,577, filed Jul. 12, 1993 now abandoned.

BACKGROUND OF THE INVENTION

The present invention relates to an orthodontic appliance, and in particular to an appliance which accommodates multi-racial dentition characteristics.

Various devices and methods have been proposed and used for correcting overcrowding of the teeth and for modifying jaw shapes in order to provide improved teeth placement. Oftentimes metallic bands and wires are used in the permanent dentition stage to provide the desired tooth straightening.

It is also known to use removable appliances in place of metallic bands and wires in order to provide orthodontic tooth positioning treatment and jaw shaping functions. Such removable appliances are generally formed in a U-shape with an upper tooth receiving trough and a lower tooth receiving trough. The appliances are preformed to accommodate various sizes of jaws and dentitions.

It has been recognized that treatment may begin prior to a time at which all deciduous teeth have been replaced by their corresponding permanent teeth through the use of removable appliances such as those disclosed in my U.S. Pat. Nos. 4,139,944 and 4,898,535.

SUMMARY OF THE INVENTION

The present invention provides an improved appliance which can be used by members of different racial groups including Caucasoid, Mongoloid and Negroid. Various enhancements and added features are provided which accommodate usage by the different racial facial characteristics and jaw and mouth constructions. A permanent dentition version appliance will maintain or move erupted permanent incisors, canines, premolars and second molars into the proper arch form accounting for the slightly larger Mongoloid and Negroid arch sizes as compared to the Caucasoid arch sizes. A mixed dentition version will guide erupting permanent incisors, canines, premolars and first molars into the proper arch form. The mixed dentition appliance is also designed to capture high-labially inclined erupting canines and gradually bring them back into a slightly larger arch circumference. A deciduous dentition version will maintain or move deciduous incisors, canines and molars into the proper arch form.

The appliances preferably are preformed in a range of sizes to accommodate various mouth sizes. The arch sizes, flange dimensions and individual tooth socket dimensions and placement are predetermined to accommodate the various mouth sizes.

There are significant correlations between tooth sizes that enables one to calculate rather accurately shapes of teeth relative to each other even before they have erupted into the mouth. Thus, with respect to mixed dentition appliances, this enables a plurality of sizes to be designed such that one is selected from the sizes of the anterior teeth that will accurately fit the permanent posterior teeth and canines as they erupt through tissue and guide them to their correct places.

The margins of the labial flanges in the area of the incisors are positioned at a higher elevation than previously available appliances by up to 0.1 to 10 millimeters. This results in an upper margin of the flange about 10 to 20 mm above the incisal edge of the central incisor. This enables the appliance to remain in place while sleeping and prevents it from slipping distally and thereby acts in the correction of overjets. With mixed dentition appliances this positions the upper margin high enough to guide canines which erupt labially and are considerably superior to the normal erupting position. This oftentimes occurs in individuals with constricted upper arches and/or slightly larger teeth frequently seen in Negroid and Mongoloid dentitions. This appliance will more easily guide such teeth into position.

This improved appliance will be able to guide, straighten, rotate and adjust the positions of various groups of teeth such as (a) the upper four permanent incisors;

(b) the lower four permanent incisors;

(c) the upper left posterior segment of permanent canines, bicuspids and molars (for permanent dentitions) and deciduous canine and molars (for deciduous and mixed dentitions) and also the upper first left permanent molar (for mixed dentitions);

(d) the upper right posterior segment of permanent canines, bicuspids and molars (for permanent dentitions) and deciduous canine and molars (for deciduous and mixed dentitions) and also the upper first right permanent molar (for mixed dentitions);

(e) the lower left posterior segment of permanent canines, bicuspids and molars (for permanent dentitions) and deciduous canine and molars (for deciduous and mixed dentitions) and also the lower left permanent molar (for mixed dentitions); and (f) the lower right posterior segment of permanent canines, bicuspids and molars (for permanent dentitions) and deciduous canine and molars (for deciduous and mixed dentitions and also the lower right permanent molar (for mixed dentitions).

Maintaining the position or moving the position of each permanent incisor, canine, bicuspid, and molar in the mouth by controlling their labial-lingual and buccal-lingual positions is provided by the improved permanent dentition appliance while guiding each permanent canine and bicuspid into the mouth is provided by the improved deciduous and mixed dentition appliance.

The upper and lower arches are controlled as a whole by allowing each to act upon the other by the elongated upper labial margin in the area of the upper four permanent incisors and the excessively-elongated lingual margin of the lower lingual flange relative to the lower four permanent incisors. The upper margin is 0.1 to 10 millimeters higher than in conventional appliances so that it places constant distillizing guidance against the pre-maxilla especially helpful in excessive overjets frequently found in Mongoloid, Negroid and Caucasoid dentitions. As the mouth opens at night during sleep, the appliance will not slip distally past the upper incisors. When the appliance remains in place, the overjet is more ideally corrected.

The lower lingual margin is excessively (0.1 to 10 millimeters) extended gingivally lingual to the lower four permanent incisors to prevent the mandible from slipping distally past the appliance while the patient is sleeping. This also helps in correcting the overjet more effectively in these same racial groups.

The lingual flange in the area of the upper four incisors has alterations on the surface engaging the lingual side of the incisors to accommodate for characteristics in the Mongoloid incisors called shovel-shaped incisors. The very incisal area (the last two millimeters of the centrals and two and one-half millimeters of the laterals incisally) of the labial flange is formed straight across and the incisal edge is in the range of 0.5–2 millimeters thick labial-lingually so that excessive pressure is placed both vertically and rotationally for all Mongoloid, Caucasoid and Negroid upper incisors. Gingivally from this straight across incisal region, the incisors take on a different shape. Slight depressions or recesses are provided lingually in the flange on both lateral sides of the central and lateral incisors to accommodate the "shovel shaped" anatomy of the typical Mongoloid upper incisal dentition. A slight bulge of 0.1–2 millimeters at each lateral side of the incisors occurs frequently in Mongoloid dentitions. Therefore, recesses of 0.1 to 2 mm which extend laterally slightly are provided so that cleats are more easily placed in this area. The area is designed, due to the thickness, to be able to fit both the Caucasoid and Negroid as well as the Mongoloid dentitions.

The varying width at the bi-canine area in the lower arch for the various sizes of appliances is from 24 to 33 millimeters, while the upper canine-to-canine distance varies from 28 to 38 millimeters. This larger dimension is also carried back distally through the last molar on both the lower and upper troughs.

DETAILED DESCRIPTION OF THE PREFERRED EMBODIMENTS

Figures 1, 1A, 1B:
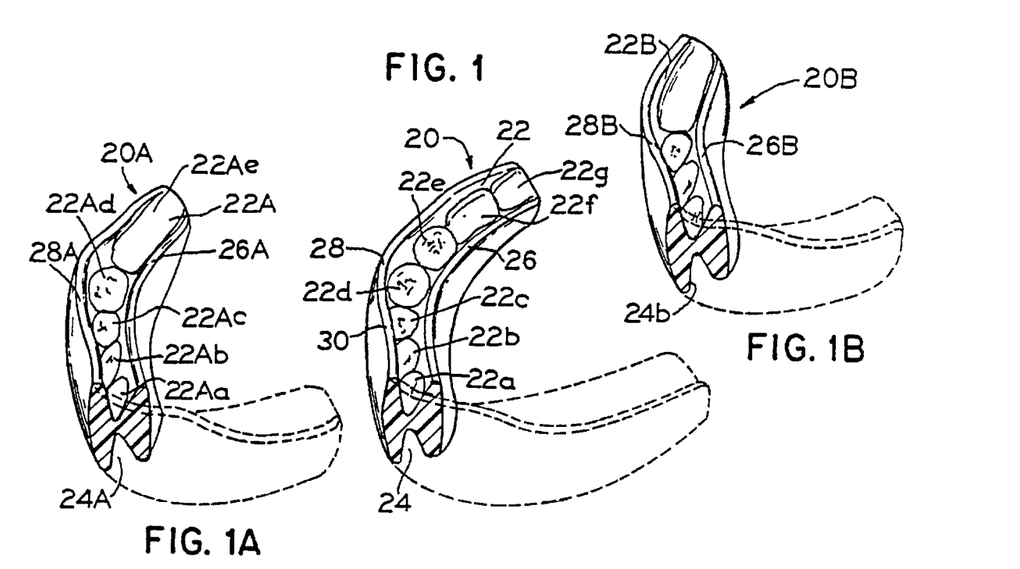
FIG. 1 is a perspective view partially cut away of a permanent dentition orthodontic appliance embodying the principles of the present invention.
FIG. 1A is a perspective view partially cut away of a mixed dentition orthodontic appliance embodying the principles of the present invention.
FIG. 1B is a perspective view partially cut away of a deciduous dentition orthodontic appliance embodying the principles of the present invention.

A preformed appliance for straightening and guiding teeth and providing jaw shaping functions for the permanent dentition is illustrated generally at 20 in FIG. 1. An appliance for the mixed dentition is illustrated generally at 20A in FIG. 1A and for the deciduous dentition generally at 20B in FIG. 1B. Each of the three types are very similar in construction, differing primarily in the distal length of the device (permanent extends to cover at least a part of the second permanent molar, mixed extends to cover the first permanent molar and the deciduous extends to cover the deciduous molars). The sizes of the devices obviously vary to accommodate varying jaw sizes, but in most other respects, the construction is the same, so the description of each of the appliances will be described with reference to the permanent dentition appliance of FIG. 1 unless specific differences pertain.

The appliance or retainer is generally U-shaped in plan view so as to conform to typical human mouth configuration and is generally H-shaped in cross section providing an upper or superior tooth receiving trough 22 and a lower or inferior tooth receiving trough 24. The sides of the troughs 22 and 24 are bounded by a lingual flange 26 which covers the tongue-surface or lingual side of the teeth of the upper and lower arch and a labial and buccal flange 28 which covers the front and cheek-facing surface of the teeth of both arches.

Both the superior and inferior tooth receiving troughs 22, 24 are provided with a plurality of tooth receiving depressions or sockets such as 22a, 22b, 22c, 22d, 22e, 22f and 22g, of different configurations for receiving the different teeth of the mouth from the central incisors through the cuspids, bi-cuspids and terminates approximately half way across the second molar. Alternatively, the appliance can of course be made having only a upper trough 22 or only a lower trough 24.

In the mixed dentition appliance 20A, both the superior and inferior tooth receiving troughs 22A, 24A are provided with a plurality of tooth receiving depressions or sockets such as 22Aa, 22Ab, 22Ac, 22Ad and 22Ae, of different configurations for receiving the different teeth of the mouth from the central incisors through the cuspids first bicuspids, deciduous second molars and terminates at the first permanent molar. Alternatively, the appliance can of course be made having only a upper trough 22A or only a lower trough 24A.

In the deciduous dentition appliance 20B, both the superior and inferior tooth receiving troughs are provided with a plurality of tooth receiving depressions or sockets of different configurations for receiving the different deciduous teeth of the mouth from the central incisors through the cuspids, first deciduous molars and they terminate at the second deciduous molar.

This appliance can be formed to be stiff or flexible, and when flexible can allow for some movement or changes to the shape of the appliance. In the embodiment illustrated in FIGS. 1, 1A and 1B, it does not otherwise have any parts moveable relative to one another. If two troughs are provided, they remain fixed relative to one another.

Figure 15:
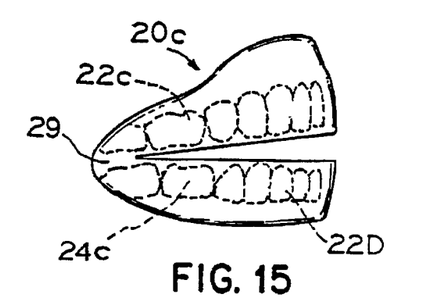
FIG. 15 is a side elevational view of an alternate embodiment of an orthodontic appliance embodying the principles of the present invention.

In the embodiment illustrated in FIG. 15, an appliance 20c is provided which is formed as a split body, one piece member, and in addition to being flexible, and thus allowing some movement or changes to the shape of the appliance, the two troughs 22C, 24C are allowed to move relative to one another by means of a hinge connection 29 provided at a distal end of each trough. The hinge connection is formed such that the device is self-opening, that is, the anterior portions are urged away from one another. An appliance of this type can be used either with permanent dentition, mixed dentition or deciduous dentition.

Such an appliance can be constructed by slitting the plastic or other resilient material appliance along a center parting line (along the direction of the occlusal plane) either at the time of molding or afterwards. If the slit is made at the time of molding, the appliance is immediately spread open and the molded plastic is allowed to cool and thermoset in an opened position so that it takes force to reclose it. The resiliency of the appliance will cause the appliance to be self-opening.

Another method of constructing such an appliance requires the appliance to be cold slit along the same center parting line after the appliance has been molded and has cooled and held open while the plastic at the "hinge" portion is heated up slightly and allowed to thermoset in the opened position. The severity of the cut towards the back or posterior section of the appliance provides for either a weak (further posterior cut) or a strong force to close the appliance on the part of the patient.

The advantages of such an appliance are not only to increase the number of children who can normally keep it in their mouths at night, but also to place a slight depressive force against the anterior (front) teeth in order to correct deep or severe overbites while the users have the appliance in their mouths. This depressive force can also be increased by inserting a flexible and resilient metal plate or spring as a hinge to increase the force necessary to close the mouth when the appliance is in the mouth.

Another advantage of the appliance where the piece is molded with the two halves separated in a flat position with an integral injection molded hinge in between, is that different configurations of dies can be placed in combination with each other as well as moved forward or backward in relation to the bendable portion of the hinge in order to increase or decrease the distance or relation anteriorly or posteriorly (front to back) and thereby create different types of appliances that can correct different severities of malocclusions such as severe Class II, mild Class II, Class I or Class III malocclusions. The hinge portion can also be made thicker or thinner, or wider or narrower, to increase or decrease the force of the hinge.

The appliance illustrated in FIG. 1 is to be used in a permanent dentition stage meaning that all deciduous teeth have been replaced with permanent teeth.

Figure 4:
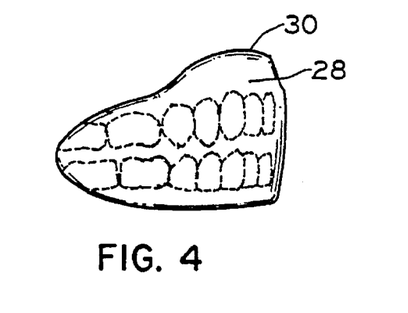
FIG. 4 is a side elevational view of the appliance of FIG. 1.

The mixed dentition appliance 20A of FIG. 1A is to be used in a mixed dentition stage meaning that some deciduous teeth have been replaced with permanent teeth, but not all. The sockets provided from the first bicuspid forward (22Aa–22Ad) are the size and in the position of the permanent teeth (FIG. 4) which may not have yet erupted. The large sockets 22Ae distal to the first bicuspid are the size of the deciduous second molar and permanent first molar combined.

The deciduous dentition appliance 20B of FIG. 1B is to be used in a deciduous dentition stage meaning that none of the deciduous teeth have been replaced with permanent teeth. The sockets provided are the size and in the position of the permanent teeth to cause the jaw to expand to the proper desired final size.

The appliance illustrated in FIG. 1 (and also the appliances of FIG. 1A, FIG. 1B and FIG. 15) varies from previously available appliances in that an upper margin 30 (FIGS. 1, 3 and 4) of the labial flange 28 extends gingivally from a tooth receiving surface 32 of the trough 22 to a greater extent than previously provided in these types of appliances. This extension beyond which has not been previously available is by an amount of 0.1 to 10 mm so that the labial flange will place constant distillizing guidance against the pre-maxilla and will overlie the gingival labial tissue. This extended margin of the flange continues laterally at least to the canines so that when canines erupt labially and are considerably superior to the normal erupting position, the appliance will more easily guide such teeth into position, if being used as the permanent canines erupt. Since previously available appliances had a labial upper flange of up to 10 mm, the present invention contemplates an upper labial flange vertical dimension of 10 to 20 mm.

Similarly, the lower lingual flange has a margin 34 (FIGS. 2 and 3) which is extended gingivally lingual 0.1 to 10 mm beyond that previously provided. This extended margin helps to prevent the mandible from slipping distally past the appliance while the patient is sleeping. Such an arrangement also helps in correcting the overjet more effectively. Thus, the present invention provides for a flange up to 14 or more millimeters from the lower lingual margin and up to 22 mm from the incisal edges of the lower incisors.

Figure 2:
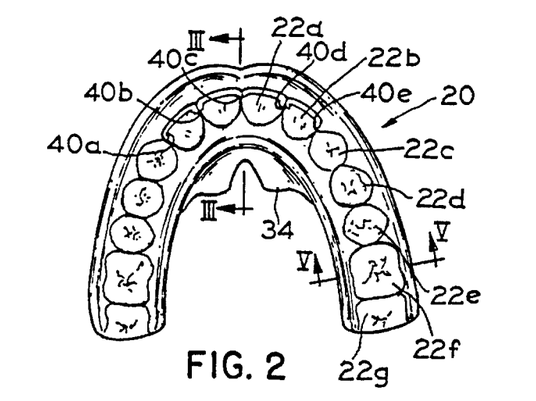
FIG. 2 is a plan view of the appliance of FIG. 1.

As seen in FIG. 2, the upper lingual flange 26 has a plurality of slight recesses 40a, 40b, 40c, 40d, 40e, each extending 0.1 to 2 mm lingually in the incisor area of the appliance. A central or mesial recess 40c is positioned at the mesio-lingual area of the central incisors and extends slightly distally to provide clearance towards the center of each of the central incisors. The next distally spaced recesses 40b, 40d are positioned at the disto-lingual edge of the central incisors and the mesio-lingual edge of the lateral incisors. These recesses 40b, 40d also extend slightly mesially to provide clearance toward the center of the central incisor and distally to provide clearance toward the center of the lateral incisors. Finally, the distal-most recesses 40a, 40e are positioned at the disto-lingual edge respectively of the lateral incisors. Thus, both mesial and distal edges on the lingual side of all four incisors are received in the recesses. These recesses are provided particularly to accommodate characteristics in the Mongoloid incisors called shovel shaped incisors. The wideness of the recesses allow for cleats to be more easily placed in these areas. The recesses terminate short of the incisal area of the flange which represents the last 1.0–3.0 mm incisally of the flange. Cleats can be placed in this area to rotate Caucasoid and Negroid teeth.

The lingual flange at the area of each recess is in the range of 0.5 to 2 mm thick labial-lingually so that excessive pressure is placed both vertically and rotationally on the upper incisors. Since the appliance preferably is fabricated of a resilient plastic material, the resiliency of the material itself will provide the desired pressures on the teeth.

Figure 3:
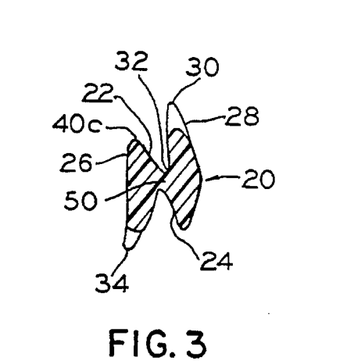
FIG. 3 is a sectional view taken generally along line III—III of FIG. 2.

Many other features and arrangements may be incorporated within either the permanent, mixed or deciduous dentition appliances described above in either the single body or split body embodiments. For example, the appliance may be fabricated in a manner to correct for overbite. In order to do this, the thickness of an isthmus 50 extending between the labial-buccal and lingual flanges is varied from that thickness wherein all occlusal surfaces contact substantially concurrently. The thickness is increased in the area of the anterior teeth (incisors) (FIG. 3) relative to the area of the posterior teeth (molars) (FIG. 5) on both sides so that the anterior teeth contact the isthmus 50 first, whereby a depressive force urges the anterior teeth into the gum as the patient attempts to continue to occlude his teeth until the posterior teeth in fact engage. This variation of the isthmus 50 thickness for the correction of the overbite can be accomplished either by reducing the thickness in the area of the posterior teeth (FIG. 5) or increasing the thickness in the area of the anterior teeth (FIG. 3).

Figure 5:
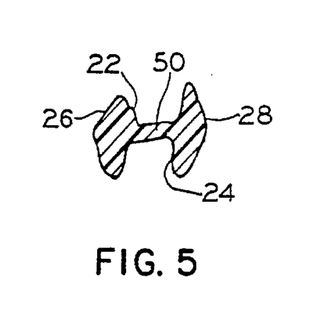
FIG. 5 is a sectional view taken generally along line V—V of FIG. 2.

However, in view of the fact that the isthmus 50 is already quite thin in the area of the posterior teeth (for example 1.5 mm) it might often be inadvisable to further reduce the thickness at this location so that it would be preferable to effect this variation by increasing the thickness of the isthmus at the anterior teeth. It has been found that an increase in the thickness at the anterior region relative to the posterior region as compared with the normal concurrent occlusion design would optimally be between 4 and 5 mm, thereby causing the anterior teeth to be depressed 1 to 2 mm before contact of the posterior teeth is possible. This arrangement is applicable for either the maxillary or mandibular teeth and can be used in the upper trough 22 and/or the lower trough 24 of an appliance having such an upper and lower trough or in the single trough of a maxillary only or mandibular only trough appliance. The trough could be increased several millimeters to say 10 to 18 mm, however the rear portion would still be only about 2 to 3 mm less than this amount or 7 to 16 mm thick.

The appliance 20 can also be used to correct for open bite and/or retain a previous correction for open bite. Open bite is essentially the opposite of overbite. In this condition the maxillary anterior teeth do not extend downwardly over the front surfaces of the mandibular anterior teeth by a sufficient amount. In accordance with this arrangement, such open bite can be corrected and/or a previous correction for open bite can be retained by simply reversing the variation made for overbite. In this case, the thickness of the isthmus 50 would be increased in the posterior region relative to the anterior region as compared to the thickness of the isthmus when all teeth engage the isthmus substantially concurrently. This would have the effect of exerting depressive forces on the prematurely contacting posterior teeth as the patient attempts to continue occluding the anterior teeth after initial occluding engagement of the posterior teeth. The effect of successful depression of the posterior teeth would of course be that the maxillary anterior teeth could then move farther down over the mandibular anterior teeth before occlusion of the posterior teeth, thereby effecting a correction of open bite. As with the overbite correction, the increase in thickness would optimally cause a premature contacting (in this case of the posterior teeth) of between 1 and 2 mm to correct for the anterior open bite.

As illustrated in the embodiments shown in FIGS. 6–9, the inner surfaces of the appliance may be modified after it has been used to bring the teeth into a desired alignment by reshaping selected tooth depressions 58 exactly to the outer contour of their respective teeth, to thereby firmly hold those selected teeth in a precise position. This reshaping is accomplished by introducing into the selected depressions a soft moldable material 60 which has the property of hardening at body temperature after a short period of time and adhering permanently to the appliance itself. With this material, the appliance is placed into the patient's mouth, centered properly therein, and the patient is asked to close his teeth and hold them together for a few minutes until the material hardens. The appliance is then removed and when the material has completely hardened it is trimmed at the margins of the tooth depressions. As a result, there is provided a tooth appliance originally preformed or custom-made for the purpose of moving teeth to a desired position, and further including a liner material within selected tooth depressions, which liner is shaped essentially precisely to the outer contour of the tooth received therein, thereby firmly holding this tooth in the position which it has reached up to this point. The use of liner material is applicable of course to either a maxillary appliance, a mandibular appliance or a combined maxillary-mandibular appliance.

The material of the liner may be one that becomes relatively hard at body temperature or one which is relatively resilient or rubber-like at body temperature. If a hard material is used, it has the advantage that the appliance will snap in place quite firmly as the occlusal surfaces of the teeth move into their respective depressions, pushing aside the hard material at the gingival edges of the depressions which are provided for pressing against the undercut portions of the teeth adjacent the gums when the teeth are firmly in place in their respective depressions. Alternatively, if the liner material is relatively resilient, it might not have the same firm positive action as with the harder material but apparently with a resilient material it is possible to more closely and precisely fit the outer contour of the teeth. Indeed, the advantages of both the hard and the soft materials can be achieved in a single embodiment utilizing a material which is hard at body and room temperature but which becomes rubbery a few degrees thereabove. This material can have the advantages of both in that the patient can warm the finished realigned appliance in hot water, place it in his mouth, after which it will slowly harden and function like the hard liner material by firmly holding the teeth in place.

Many materials are known which could be utilized to form the liner material. Preferably, materials would be used which would polymerize, chemically bond with or otherwise strongly adhere to the material of the appliance itself or with an additional material applied thereto for that purpose. For example, the preformed or custom made appliance could be made of a polymer or copolymer of the same material or of a material which would provide an adhering surface for the insert material. This might include for example a material with a small percentage by weight of acrylic resin which would thus provide a perfect adhering surface for a self-cure acrylic polymer which would remain permanently attached thereto. A methyl-methacrylate monomer may be painted on the surface of the appliance where the liner material is to be added, after which this monomer and the self-cure acrylic polymer are mixed into a runny consistency and placed onto the painted surface. With the appliance in this state, the appliance would be placed into the patient's mouth, centered properly, and the patient would be asked to close his teeth and hold them together for a couple of minutes until the material hardens. After hardening, the material would be trimmed and polished.

Figure 6:
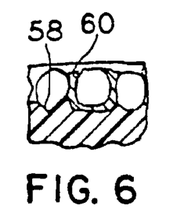
FIG. 6 is a partial lateral sectional view of an alternate embodiment of the appliance of FIG. 1.
Figure 7:
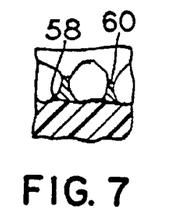
FIG. 7 is a partial sectional view similar to FIG. 6 with a tooth engaged in the appliance.
Figure 8:
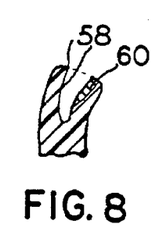
FIG. 8 is a partial side sectional view of the embodiment of FIG. 6.
Figure 9:
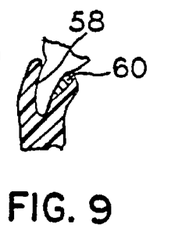
FIG. 9 is a partial side sectional view similar to FIG. 8 with a tooth engaged in the appliance.

FIGS. 6 and 8 illustrate the upper lateral incisor tooth depression with the liner material therein. In FIG. 6 the liner material is shown as it might extend slightly up into the space between this tooth and its adjacent tooth while FIG. 8 illustrates how the material might run up to the upper edge of the depression so as to mate with the undercut portions of the labial and lingual sides of the tooth. FIGS. 7 and 9 illustrate the modified depressions of FIGS. 6 and 8 with a lateral incisor tooth located therein.

Figure 10:
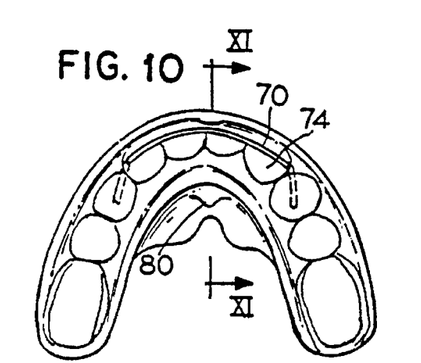
FIG. 10 is a plan view of an alternate embodiment of the appliance of FIG. 1.
Figure 11:
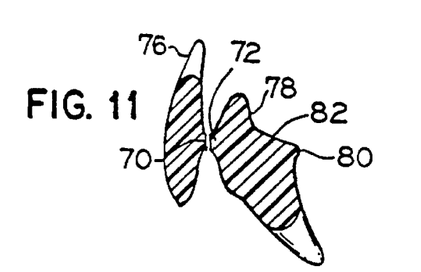
FIG. 11 is a side sectional view taken generally along the line XI—XI of FIG. 10.

FIGS. 10–11 illustrate another embodiment of the present invention in which a vertical slit 70 is provided in the isthmus 72 in the region of the sockets 74 for at least the incisors as shown in solid lines and, in some cases to include the socket region for the canines (usually for adult usage) as illustrated by dashed lines. It should be understood that the slit 70 may be a through-slit which extends completely through the appliance, or it may be an opposed pair of channels or recesses or a partial slit so long as it is sized and shaped to allow the teeth to erupt vertically without resistance. In this manner the isthmus 72 interconnects the flanges 76, 78 only in the posterior portion of the appliance and does not interconnect the flanges in the anterior portion. The vertical slit 70 ensures that no pressure will be applied to the incisors (and possibly canines) in a vertical direction when the user of the appliance bites thereon. The isthmus 72 which is solid in the region of the posterior teeth will prevent further eruption of those teeth while the slit will encourage further eruption of the anterior teeth to assist in the correction of the open bite condition.

This embodiment also includes a molded inset 80 which preferably is molded integrally with the appliance, the inset being molded to the lingual region of the appliance as a reminder guide for the tip of the tongue. The inset 80 includes one or more pointed protrusions which may be positioned along the lower midline portion of the appliance or laterally spaced from the midline, on the lingual side, to discourage the tongue from assuming an anterior and depressed position. The contour of the appliance along the midline, as best seen in FIG. 11, also includes a recessed area 82 superior to the protrusions which encourages the tongue to assume a higher vertical position especially when used in combination with the pointed protrusions. The addition of this molded inset 80 serves to encourage proper tongue positioning, thereby overcoming the anterior tongue thrust problem which tends to worsen the open bite condition.

Figure 12:
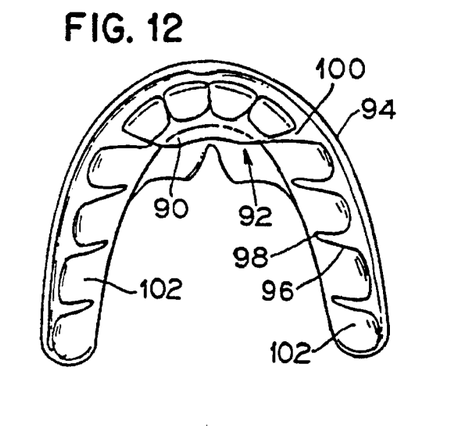
FIG. 12 is a plan view of an alternate embodiment of the appliance of FIG. 1.
Figure 13:
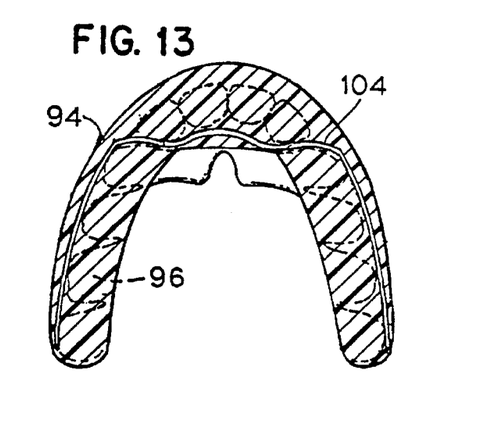
FIG. 13 is a sectional view through the appliance of FIG. 12.
Figure 14:
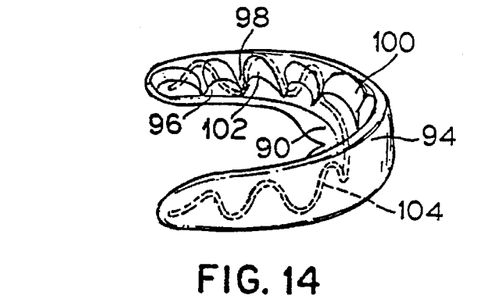
FIG. 14 is a perspective view of the appliance of FIG. 12.

A further embodiment is illustrated in FIGS. 12-14. In this embodiment the lingual flange 90 is provided at an anterior bight portion 92 of the U-shaped appliance to overlie a lingual surface of at least one of an upper or lower set of central and lateral incisors. The lingual flange terminates prior to the canine so that the patient's tongue will be free to engage the lingual surface of the posterior teeth (canines and molars). The labial/buccal flange 94 may be configured so as to hold the cheeks and lips away from the buccal and labial surfaces of the patient's teeth.

The appliance preferably is a preformed or custom-made device fabricated of a molded resilient material such as plastic that conforms to the anterior teeth (central and lateral incisors) and, the buccal flange 94 is spaced laterally away from the posterior teeth. Thus, the force of the tongue against the posterior teeth causes these teeth to move buccally to gain extra room for the patient's crowded or potentially crowded teeth.

A lingual surface 96 of the buccal shield is notched in that it has lingually extending projections 98 extending therefrom. The projections 98 are positioned to project into the interproximal spaces between each of the posterior teeth and a wedge-shaped projection 100 is provided between the canines and the lateral incisors. The projections are angled anteriorly and lingually from their points of attachment at the buccal flange to thereby define a buccally and posteriorly directed slot or pocket 102 for receiving each of the posterior teeth. A slanting of the projections encourages each buccal tooth to assume an expanded position while gaining space anteriorly between the canine and the lateral incisors where the space can be used for the elimination of crowding in the anterior segment, especially in the lateral-canine area. Preferably the expansion of the buccal shield allows for approximately 1 to 20 mm of expansion between the canines in the upper and lower arches as well as approximately 1–20 mm of lateral expansion between each of the molars. Expansion may be provided for the anterior segment if desired or needed, but in some instances no anterior segment expansion would be required.

The wedged shaped projection 100 between the lateral incisors and the canines causes the canines to drift distally along a distal surface of the wedge to assume a more expanded but slightly distal position. As each tooth distal of the canine is expanded, it in turn migrates slightly distally or at least does not move mesially as it expands. In this way, the excess space created by the posterior expansion ends up in the lateral-canine area.

It may also be preferable to include a wire member 104 molded into the interior of the appliance to assist in maintaining the desired buccal expansion dimension or other configuration of the appliance. The wire may have a serpentine shape as best seen in FIG. 14 to permit adjustments of the appliance horizontally as well as vertically or a combination of horizontal and vertical in a compound bend.

The appliance embodying the present invention may be provided with a means for determining the amount of usage of the appliance by the patient. A specific problem facing the orthodontist is that of obtaining full cooperation of the patient in utilizing the device. On occasion, a patient having been instructed to wear an appliance for certain periods of time each day will return to the orthodontist's office at which time the orthodontist will observe that the progress in terms of movement of teeth has not been satisfactory. It is critically important that the orthodontist be aware of the reason for such insufficient progress. Specifically, it might be because of an individual resistance to tooth movement, an improperly fitting appliance or simply due to the fact that the patient does not wear the appliance as instructed. Thus, the appliance may be formed of a material such that under normal conditions it is essentially transparent, but wherein the appliance has the characteristic of changing opacity in proportion to the time the appliance is in the mouth. As a result thereof, if a patient returns to the orthodontist office with insufficient progress, the orthodontist can then simply visually inspect the appliance to determine whether or not the patient has in fact been using the appliance.

Although there are perhaps many materials with which the appliance may be made, in a preferred embodiment, the material of the appliance is a soft pliable plastic that softens and melts at rather high temperatures. Early plastics were known to have the disadvantage that they absorbed moisture and became cloudy. This is known as water-blush plastic. Over the years, however, many varieties of plastics were developed including means for eliminating this water-blush characteristic such that they remain transparent even when subjected to high moisture conditions.

In the preferred embodiment the appliance is made by mixing together a proportion of water-blush and a portion of non-water blush plastic. The proportion of water-blush to non-water blush plastics can be varied quite widely, however the proportion should preferably be selected so as to retain at least some transparency as a diagnostic aid even during full cooperation.

In addition, the proportion should of course be selected with direct reference to the period of time that it is contemplated the patient will be instructed to wear the appliance. That is, the proportions should be chosen such that after the correct time of wear, the appliance will have a high level of opacity consistent with the need for a certain degree of transparency.

It has been determined that a range from about 25% water-blush to about 75% water-blush plastic provides both meaningful indication of wear as well as the necessary transparency.

The appliance may also be made of a molding consisting of a moldable base material, the moldable base material being sufficiently absorptive to permit a recharging of the appliance with fluoride by soaking the appliance in a fluoridating material. The base material may be made of an absorbent blush plastic admixed prior to melting and shaping with a fluoridating material and a concentration varying from 0.01 milligrams to 200 milligrams per milliliter or 0.01% to 70% by weight. A recharge of fluoride may be given to the appliance periodically or there can be an alternative method of delivery by soaking the appliance in the fluoride compound. Certain areas of the appliance can also be soaked such as only around the tooth areas by placing the chemicals into the sockets and allowing them to be absorbed into the soluble type plastic. In this way, the fluoride chemicals are mostly present at the tooth surface and not on the cheek surface so any potential irritation on the cheeks is avoided.

As is apparent from the foregoing specification, the invention is susceptible of being embodied with various alterations and modifications which may differ particularly from those that have been described in the preceding specification and description. It should be understood that I wish to embody within the scope of the patent warranted hereon all such modifications as reasonably and properly come within the scope of my contribution to the art.

I claim as my invention:

1. An orthodontic appliance which is preformed to be generally U-shaped in plan view and includes a preformed tooth receiving trough formed between lingual and labial/buccal side flanges in at least an upper side thereof, which trough includes prefabricated tooth receiving depressions of predetermined dimensions for receiving and positioning teeth from central and lateral incisors to and including at least a molar, said appliance, trough and depressions being preformed of said predetermined dimensions without reference to a particular patient's dentition, said labial/buccal flange, in an area adapted to engage said incisors, extending gingivally from a tooth receiving surface of said trough by more than 10 mm so as to constantly engage a patient's gingival labial tissue and place constant distillizing guidance against a patient's pre-maxilia, said lingual flange having laterally spaced apart, vertically oriented lingually extending recesses of 0.1 to 1 mm in depth which extend slightly laterally at a mesial area and a distal edge of the central incisors and at a distal edge and a mesial edge of the lateral incisors so as to be positioned adjacent to the lateral edges of a lingual side of all four incisors, said recesses being defined by adjacent portions of said lingual flange which are not recessed and which are adapted to engage the lateral edges of the lingual side of all four incisors.

2. An orthodontic appliance according to claim 1, wherein said appliance includes upper and lower troughs and said lingual flange defining said lower trough extends gingivally and lingually more than 8 mm in the area of said lower incisors.

3. An orthodontic appliance according to claim 1, wherein said upper lingual trough has laterally spaced apart, vertically oriented lingually extending recesses of 0.1 to 1 mm which extend slightly laterally at a mesial area and distal edge of the central incisors and at a distal edge and mesial edge of the lateral incisors so as to overlie the lateral edges of all four incisors.

4. An orthodontic appliance according to claim 3, wherein said upper labial flange at said recesses is 0.5 to 2 mm thick labial-lingually.

5. An orthodontic appliance according to claim 1, wherein said appliance comprises a molding consisting of a moldable base material, said moldable base material being sufficiently absorbative to permit a recharging of the appliance by soaking the appliance in fluoridating material, and wherein said base material is an absorbent blush plastic admixed prior to melting and shaping with a fluoridating material in a concentration varying from 0.01 mg. to 200 mg. per milliliter or 0.01% to 70% by weight.

6. An orthodontic appliance according to claim 1, wherein said appliance is formed of a material which is normally essentially transparent under normal room conditions and which increases in opacity by absorption of moisture when placed in a patient's mouth for a predetermined period of time.

7. An orthodontic appliance according to claim 1, wherein said flanges are connected by an isthmus, a thickness of said isthmus being greater at an anterior portion of said appliance than at a posterior portion such that as the side thereof opposite the trough rests against the occlusal surfaces of the row other than said one row, the anterior teeth of said one row engage the isthmus before the posterior teeth of said one row to exert a force against the anterior teeth depressing them into the gum to correct for overbite or to retain a previous overbite correction as the posterior teeth complete their movement towards engagement with the isthmus.

8. An orthodontic appliance according to claim 1, wherein said flanges are connected by an isthmus, a thickness of said isthmus being greater at a posterior portion of said appliance than at an anterior portion such that as the side thereof opposite the trough rests against the occlusal surfaces of the row other than said one row, the posterior teeth of said one row engage the isthmus before the anterior teeth of said one row to exert a force against the posterior teeth depressing them into the gum to correct for open bite or to retain a previous open bite correction as the anterior teeth complete their movement towards engagement with the isthmus.

9. An orthodontic appliance according to claim 1, wherein said appliance is formed of an elastomeric material, and said trough has one or more selected depressions therein shaped substantially precisely to the outer contour of a respective tooth sufficiently to hold said respective tooth in a fixed position relative to said appliance, said appliance comprising a substrate in the shape of a conventional appliance shaped to correct and retain teeth within the patient's mouth, and including a liner forming a discontinuous phase with respect to the substrate within the selected one or more depressions to form the portion of outer contour of said selected teeth.

10. An orthodontic appliance according to claim 1, wherein said flanges are connected by an isthmus, said isthmus having a vertical slit in an anterior portion of said appliance which is engaged by at least some of the central incisor, lateral incisor and canine anterior teeth.

11. An orthodontic appliance according to claim 1, wherein said flanges are connected by an isthmus and means for guiding the tongue including at least one pointed protrusion formed on the lingual side of the lower midline portion of the appliance and a recessed area superior to the protrusion for receiving a tip of the tongue.

12. An orthodontic appliance according to claim 1, wherein said buccal flange includes a plurality of projections defining tooth receiving slots therebetween extending longitudinally from said buccal flange, said projections being spaced to project between each of the posterior teeth of the patient.

13. An orthodontic appliance according to claim 1, wherein said appliance includes at least one wire molded therein for retaining said appliance in a desired shape.

14. An orthodontic appliance according to claim 1, for use with a permanent dentition, wherein said appliance extends posteriorly to a position to engage a second permanent molar.

15. An orthodontic appliance according to claim 1, for use with a mixed dentition, wherein said appliance extends posteriorly to a position to engage a first permanent molar.

16. An orthodontic appliance according to claim 1, for use with a deciduous dentition, wherein said appliance extends posteriorly to a position to engage a deciduous molar.

17. An orthodontic appliance according to claim 1, wherein said appliance is formed as a single body member with an upper trough and a lower trough permanently fixed relative to one another.

18. An orthodontic appliance according to claim 1, wherein said appliance is formed as a split body member with an upper trough and a lower trough hinged together at distal ends thereof.

19. An orthodontic appliance which is preformed to be generally U-shaped in plan view and includes a preformed tooth receiving trough formed between lingual and labial/buccal side flanges in at least an upper side thereof, which trough includes prefabricated tooth receiving depressions of predetermined dimensions for receiving and positioning teeth from central and lateral incisors to and including at least a molar, said appliance, trough and depressions being preformed of said predetermined dimensions without reference to a particular patient's dentition, said lingual flange having laterally spaced apart, vertically oriented lingually extending recesses of 0.1 to 1 mm in depth which extend slightly laterally at a mesial area and a distal edge of the central incisors and at a distal edge and a mesial edge of the lateral incisors so as to be positioned adjacent to the lateral edges of a lingual side of all four incisors, said recesses being defined by adjacent portions of said lingual flange which are not recessed and which are adapted to engage the lateral edges of the lingual side of all four incisors.

20. An orthodontic appliance according to claim 19, wherein said labial flange at said recesses is 0.5 to 2 mm thick labial-lingually.

21. An orthodontic appliance according to claim 20, wherein said appliance is fabricated of a resilient plastic material so that excessive pressure is placed both vertically and rotationally on the incisors engaged by said lingual flange.

22. An orthodontic appliance of the type which is preformed to be generally U-shaped in plan view and includes a preformed tooth receiving trough formed between lingual and labial/buccal side flanges in at least a lower side thereof, which trough includes prefabricated tooth receiving depressions of predetermined dimensions for receiving and positioning teeth from central and lateral incisors to and including at least a molar, said appliance, trough and depressions being preformed of said predetermined dimensions without reference to a particular patient's detention, said lingual flange, in an area of said incisors, extending gingivally and lingually more than 8 mm so as to overlie a patient's gingival lingual tissue and place constant correcting guidance against a patient's overjet and preclude the appliance from slipping distally past the patient's mandible, said lingual flange having laterally spaced apart, vertically oriented lingually extending recesses of 0.1 to 1 mm in depth which extend slightly laterally at a mesial area and a distal edge of the central incisors and at a distal edge and a mesial edge of the lateral incisors so as to be positioned adjacent to the lateral edges of a lingual side of all four incisors, said recesss being defined by adjacent portions of said lingual flange which are not recessed and which are adapted to engage the lateral edges of the lingual side of all four incisors.

23. An orthodontic appliance according to claim 22, wherein said appliance comprises a molding consisting of a moldable base material, said moldable base material being sufficiently absorbative to permit a recharging of the appliance by soaking the appliance in fluoridating material, and wherein said base material is an absorbent blush plastic admixed prior to melting and shaping with a fluoridating material in a concentration varying from 0.01 mg. to 200 mg. per milliliter or 0.01% to 70% by weight.

24. An orthodontic appliance according to claim 22, wherein said appliance is formed of a material which is normally essentially transparent under normal room conditions and which increases in opacity by absorption of moisture when placed in a patient's mouth for a predetermined period of time.

25. An orthodontic appliance according to claim 22, wherein said flanges are connected by an isthmus, a thickness of said isthmus being such that as the side thereof opposite the trough rests against the occlusal surfaces of the row other than said one row, the anterior teeth of said one row engage the isthmus before the posterior teeth of said one row to exert a force against the anterior teeth depressing them into the gum to correct for overbite or to retain a previous overbite correction as the posterior teeth complete their movement towards engagement with the isthmus.

26. An orthodontic appliance according to claim 22, wherein said flanges are connected by an isthmus, a thickness of said isthmus being such that as the side thereof opposite the trough rests against the occlusal surfaces of the row other than said one row, the posterior teeth of said one row engage the isthmus before the anterior teeth of said one row to exert a force against the posterior teeth depressing them into the gum to correct for open bite or to retain a previous open bite correction as the anterior teeth complete their movement towards engagement with the isthmus.

27. An orthodontic appliance according to claim 22, wherein said appliance is formed of an elastomeric material, and said trough has one or more selected depressions therein shaped substantially precisely to the outer contour of its respective tooth sufficiently to hold its respective tooth in a fixed position relative to said appliance, said appliance comprising a substrate in the shape of a conventional appliance shaped to correct and retain teeth within the patient's mouth, and including a liner forming a discontinuous phase with respect to the substrate within the selected one or more depressions to form the portion of outer contour of said selected teeth.

28. An orthodontic appliance according to claim 22, wherein said flanges are connected by an isthmus, said isthmus having a vertical slit in an anterior portion of said appliance which is engaged by at least some of the central incisor, lateral incisor and canine anterior teeth.

29. An orthodontic appliance according to claim 22, wherein said flanges are connected by an isthmus and means for guiding the tongue including at least one pointed protrusion formed on the lingual side of the lower midline portion of the appliance and a recessed area superior to the protrusion for receiving a tip of the tongue.

30. An orthodontic appliance according to claim 22, wherein said buccal flange includes a plurality of projections defining tooth receiving slots therebetween extending longitudinally from said buccal flange, said projections being spaced to project between each of the posterior teeth of the patient.

31. An orthodontic appliance according to claim 22, wherein said appliance includes at least one wire molded therein for retaining said appliance in a desired shape.

32. A series of differently sized orthodontic appliances which are each preformed to be generally U-shaped in plan view and include a preformed tooth receiving trough formed between lingual and labial/buccal side flanges in at least an upper side thereof, which trough includes prefabricated tooth receiving depressions of predetermined dimensions for receiving and positioning teeth from central and lateral incisors to an including at least a molar, said appliances, trough and depressions being preformed of said predetermined dimensions without reference to a particular patient's dentition, said labial/buccal flange in an area adapted to engage said incisors, extending gingivally from a tooth receiving surface of said trough by more than 10 mm so as to constantly engage a patient's gingival labial tissue and provide constant distillizing guidance against a patient's pre-maxilla, said lingual flange having laterally spaced apart, vertically oriented lingually extending recesses of 0.1 to 1 mm in depth which extend slightly laterally at a mesial area and a distal edge of the central incisors and at a distal edge and a mesial edge of the lateral incisors so as to be positioned adjacent to the lateral edges of a lingual side of all four incisors, said recesses being defined by adjacent portions of said lingual flange which are not recessed and which are adapted to engage the lateral edges of the lingual side of all four incisors.

33. A series according to claim 32, wherein said appliances are preformed in a range of different sizes to accommodate different sized mouths and stages of dentition.

34. The series according to claim 32 further comprising a preformed tooth receiving trough formed between lingual and labial/buccal side flanges in a lower side thereof, said lingual flange, in an area adapted to engage said incisors, extending gingivally and lingually more than 8 mm so as constantly overlie a patient's gingival lingual tissue and to place constant correcting guidance against a patient's overjet and to preclude the appliance from slipping distally past the patient's mandible.

35. A series of differently sized orthodontic appliances which are each preformed to be generally U-shaped in plan view and include a preformed tooth receiving trough formed between lingual and labial/buccal side flanges in at least a lower side thereof, which trough includes prefabricated tooth receiving depressions of predetermined dimensions for receiving and positioning teeth from central and lateral incisors to and including at least a molar, said appliance, trough and depressions being preformed of said predetermined dimensions without reference to a particular patient's dentition, said lingual flange, in an area adapted to engage said incisors, extending gingivally and lingually more than 8 mm so as to constantly overlie a patient's gingival lingual tissue and place constant correcting guidance against a patient's overjet and preclude the appliance from slipping distally past the patient's mandible, said lingual flange having laterally spaced apart, vertically oriented lingually extending recesses of 0.1 to 1 mm in depth which extend slightly laterally at a mesial area and a distal edge of the central incisors and at a distal edge and a mesial edge of the lateral incisors so as to be positioned adjacent to the lateral edges of a lingual side of all four incisors, said recesses being defined by adjacent portions of said lingual flange which are not recessed and which are adapted to engage the lateral edges of the lingual side of all four incisors.

36. A series according to claim 35, wherein said appliances are preformed in a range of different sizes to accommodate different sized mouths and stages of dentition.

* * * * *